United States Patent [19]

Sasahara et al.

[11] 4,435,391

[45] Mar. 6, 1984

[54] DIBENZOXAZEPINE DERIVATIVE, AND PHARMACEUTICAL COMPOSITION COMPRISING THE SAME

[75] Inventors: Kazuo Sasahara, Omiya; Masamitsu Honda, Tokyo; Masuo Koizumi, Tokyo; Yasushi Murakami, Tokyo; Tomohiro Neichi, Tokorozawa; Hiroshi Nakakimura, Kamakura; Yukifumi Noda; Hiroshi Matsushita, both of Tokyo; Shun-ichi Hata, Yokohama, all of Japan

[73] Assignee: Chugai Seiyaku Kabushiki Kaisha, Tokyo, Japan

[21] Appl. No.: 354,651

[22] Filed: Mar. 4, 1982

Related U.S. Application Data

[63] Continuation-in-part of Ser. No. 263,184, May 13, 1981, abandoned.

[30] Foreign Application Priority Data

May 28, 1980 [JP] Japan .................................. 55-70176

[51] Int. Cl.³ .................... C07D 273/06; A61K 31/55
[52] U.S. Cl. ................................. 424/244; 260/330.7; 542/455
[58] Field of Search ..................... 260/330.7; 424/244; 542/455

[56] References Cited

U.S. PATENT DOCUMENTS

| | | | |
|---|---|---|---|
| 3,458,516 | 7/1969 | Howell et al. | 260/330.7 |
| 3,478,056 | 11/1969 | Schmutz et al. | 260/330.7 |
| 3,676,460 | 7/1972 | Hirohashi et al. | 260/330.8 |
| 3,752,851 | 8/1973 | Winter et al. | 260/330.7 |
| 4,290,953 | 9/1981 | Koizumi et al. | 260/330.7 |

Primary Examiner—Norma S. Milestone
Attorney, Agent, or Firm—Browdy and Neimark

[57] ABSTRACT

Dibenzoxazepine derivatives of the formula:

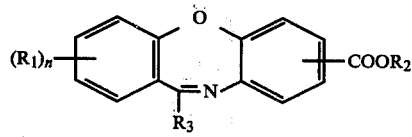

wherein $R_1$, n, $R_2$ and $R_3$ are as defined in the description, process for preparing the same, pharmaceutical composition containing the same and method of treating diseases in circulatory organs administering the composition to a patient are disclosed.

The compounds of the formula have lipid lowering activity, lipid peroxide lowering activity, blood sugar lowering activity and activity to inhibit the aggregation of platelets, and hence are useful as a medicine.

20 Claims, No Drawings

DIBENZOXAZEPINE DERIVATIVE, AND PHARMACEUTICAL COMPOSITION COMPRISING THE SAME

CROSS-REFERENCES TO RELATED APPLICATION

This application is a continuation-in-part of application Ser. No. 263,184 filed on May 13, 1981, now abandoned.

This invention relates to a dibenzoxazepine derivative of the formula:

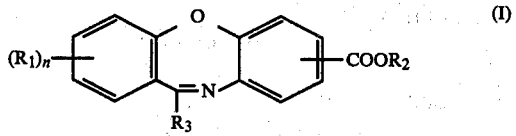

(wherein $R_1$ is a hydrogen atom, a halogen atom, a lower alkyl group or a lower alkoxy group; n is an integer of 1 or 2 provided that each $R_1$ may be different when n is 2; $R_2$ is a hydrogen atom or a lower alkyl group; $R_3$ is a hydrogen atom, a lower alkyl group, a phenyl group which may have a substituent, or a styryl group which may have a substituent), and a pharmaceutically acceptable salt thereof, a process for preparing the same, and a pharmaceutical composition containing said dibenzoxazepine derivative as an active ingredient.

According to this invention, the compound of the formula (I) can be obtained easily be cyclizing a compound of the formula (II):

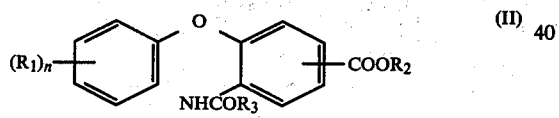

(wherein $R_1$, n, $R_2$ and $R_3$ have the same meaning as defined above). The cyclization is performed using an anhydrous inert solvent such as benzene, chloroform, toluene, xylene or chlorobenzene in the presence of a dehydrating agent such as phosphorus oxychloride, zinc chloride, phosphorus pentoxide, polyphosphoric acid or polyphosphoric acid ester at a temperature between 50° and 180° C., preferably between 80° and 130° C., for a period of from 1 to 10 hours, preferably from 3 to 5 hours.

After the cyclization, a compound of the formula (I) wherein $R_2$ is a lower alkyl group can optionally be hydrolyzed by a conventional method to form carboxylic acid wherein $R_2$ is a hydrogen.

The compound (II) used as the starting material in the cyclization is also a novel compound, and it can be easily obtained by acylating the corresponding aminodiphenyl ether derivative.

A compound of the formula (I) wherein $R_2$ is hydrogen is produced on an industrial scale, for example, by oxidizing a compound of the formula (III):

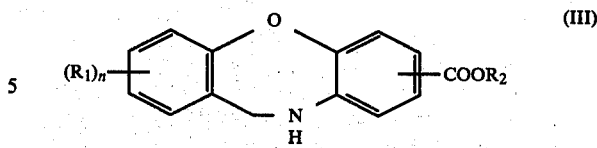

(wherein $R_1$, n and $R_2$ have the same meaning as defined above). The oxidation is performed in a conventional manner, for example, by dissolving a compound of the formula (III) in an inert solvent such as chloroform, benzene, toluene, xylene or chlorobenzene, and irradiating the solution with light or heating under reflux said compound in the presence of a dehydrogenating agent such as paraquinone or chloranil. The solution is preferably irradiated with natural light or ultraviolet rays for a period of 1 hour to 10 days that varies depending upon the nature and amount of the light used. The reaction using a dehydrogenating agent is performed at a temperature between 50° and 150° C., preferably between 80° and 140° C., for a period of from 1 to 5 hours, preferably from 2 to 4 hours.

The compound of the formula (III) used as the starting material in the oxidation is also a novel compound, and it can readily be prepared by reducing and cyclizing a diphenyl ether (VI) in a solvent such as methanol, ethanol, dioxane or tetrahydrofuran in the presence of 5 to 10% of a Raney nickel or palladium or carbon at room temperature, optionally followed by hydrolysis. The diphenyl ether (VI) is prepared through the following reaction course:

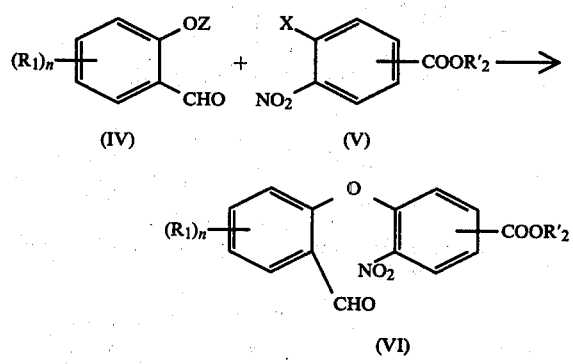

(wherein $R_1$ and n have the same meaning as defined above; Z is an alkali metal atom; X is a halogen atom; $R'_2$ is a lower alkyl group).

The compound (I) of this invention is optionally converted in a conventional manner to its pharmaceutically acceptable salt at the nitrogen atom on the dibenzoxazepine ring or at the carboxyl group when $R_2$ is hydrogen.

The compound (I) of this invention thus prepared has lipid lowering activity, lipid peroxide lowering activity, blood sugar lowering activity and activity to inhibit the aggregation of platelets, and hence is useful as a medicine.

When used as a medicine having these activities, the compound of this invention is formulated by a conventional technique and administered orally in the form of, say, a tablet, granule, powder or capsule, or parenterally in the form of an injection. For preparing a tablet, gradule, powder and capsule, lactose, starch, dextrin, sucrose, crystalline cellulose, kaolin, calcium carbonate, talc and magnesium stearate are preferably used as a pharmaceutical excipient. For preparing an injection, the compound (I) is dissolved in a solution of salt such as sodium bicarbonate or potassium bicarbonate. For oral administration, the dose is 1–2000 mg/day, preferably 5–800 mg/day, and for parenteral administration, the dose is 0.1–500 mg/day, preferably 0.5–200 mg/day, and the desired amount is administered in a single dose or in divided portions.

This invention is now described in greater detail by reference to the following Experiments and Examples to which the invention is by no means limited.

EXPERIMENT 1

Male mice of ddY strain weighing between 25 and 30 g were divided into groups of 10 members each and administered intravenously 75 mg/kg of alloxan. Twenty-two hours later, each mouse was administered orally 300 mg/kg of a test compound of this invention as suspended in 1% gum arabic. Forty-eight hours after the administration of alloxan, blood was drawn from the inferior vena cava under ether anesthesia of the animals with ether. The lipid peroxide level (TBA) of blood was determined with Lipoperoxide-Test Wako (Wako Pure Chemical Industries, Ltd., Japan). The level of blood sugar (BG) was determined with New Blood Sugar Test (Berlinger Mannheim AG., West Germany). The average percent reduction of TBA and BG of the mice treated with the compounds of this invention is set forth in Table 1 on the basis of the values for the untreated mice. As a positive control, tocopherol was used.

TABLE 1

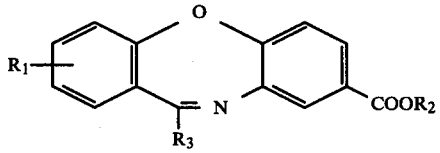

| No. | Compound $R_1$ | $R_2$ | $R_3$ | Percent Reduction TBA $\bar{x} \pm$ S.E. | BG $\bar{x} \pm$ S.E. |
|---|---|---|---|---|---|
| | α-tocopherol | | | 51.7 ± 3.7 | — |
| 1 | H | H | H | 12.3 ± 3.2 | 15.5 ± 2.5 |
| 2 | 4OCH$_3$ | H | H | 25.5 ± 3.5 | 22.4 ± 4.2 |
| 3 | 3CH$_3$ | C$_2$H$_5$ | H | 23.0 ± 4.1 | 16.5 ± 2.7 |
| 4 | 3CH$_3$ | C$_2$H$_5$ | C$_2$H$_5$ | 35.2 ± 4.3 | — |
| 5 | 3OCH$_3$ | C$_2$H$_5$ | CH$_3$ | 61.1 ± 2.5 | — |
| 6 | 3OCH$_3$ | C$_2$H$_5$ | C$_2$H$_5$ | 54.0 ± 2.9 | — |
| 7 | 3OCH$_3$ | H | CH$_3$ | 64.8 ± 2.2 | 15.7 ± 4.1 |
| 8 | 3CH$_3$ | H | CH$_3$ | 52.0 ± 3.6 | 16.3 ± 2.6 |
| 9 | 3OCH$_3$ | H | C$_2$H$_5$ | 67.7 ± 1.8 | 18.4 ± 3.1 |
| 10 | 4-OCH$_3$ | CH$_3$ | H | 50.3 ± 2.5 | — |
| 11 | 4-OCH$_3$ | C$_3$H$_7$(n) | H | 38.6 ± 4.1 | — |
| 12 | 4-OCH$_3$ | C$_4$H$_9$(n) | H | 19.7 ± 3.8 | — |
| 13 | 2-Cl | H | H | 18.3 ± 4.2 | 10.4 ± 4.6 |
| 14 | 4-OC$_2$H$_5$ | H | H | 63.4 ± 2.1 | 18.7 ± 2.8 |
| 15 | 2-CH$_3$ | H | H | 23.8 ± | 16.5 ± |

TABLE 1-continued

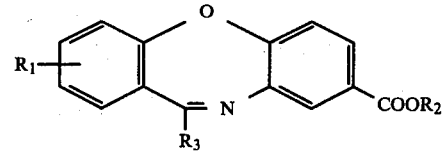

| No. | Compound $R_1$ | $R_2$ | $R_3$ | Percent Reduction TBA $\bar{x} \pm$ S.E. | BG $\bar{x} \pm$ S.E. |
|---|---|---|---|---|---|
| | | | | 3.5 | 3.5 |
| 16 | 2,4-(OCH$_3$)$_2$ | C$_2$H$_5$ | C$_2$H$_5$ | 28.5 ± 3.1 | — |
| 17 | 2-OCH$_3$ | C$_2$H$_5$ | —C=CH—C$_6$H$_5$ | 34.4 ± 2.9 | — |
| 18 | 3-OCH$_3$ | C$_2$H$_5$ | —C$_6$H$_5$ | 41.7 ± 3.2 | — |
| 19 | 3-OCH$_3$ | C$_2$H$_5$ | m-CH$_3$C$_6$H$_4$ | 34.9 ± 2.2 | — |
| 20 | 3-CH$_3$ | C$_2$H$_5$ | C$_3$H$_7$(n) | 39.6 ± 3.8 | — |

EXPERIMENT 2

The mice of ddY strain weighing between 25 and 30 g were fasted overnight and then Triton WR-1399(500 mg/kg) (Ruger Chemicals Co.) was intravenously injected into the mice. Immediately and 8 hours after the injection, each mouse was administered 150 mg/kg of a test compound of this invention as suspended in 1% aqueous methylcellulose.

24 Hours after the injection of Triton, the blood was drawn from the heart. The cholesterol (TC) and triglyuride (TG) levels of plasma were determined with RaBASuper (Chugai Seiyaku K.K., Japan). The results are shown in Table 2 below.

As a positive control, chlofibrate were used.

TABLE 2

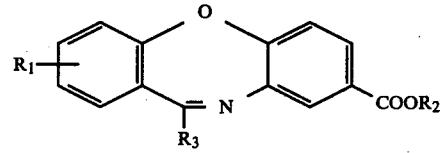

| No. | Compound $R_1$ | $R_2$ | $R_3$ | Percent Reduction TC $\bar{x} \pm$ S.E. | TG $\bar{x} \pm$ S.E. |
|---|---|---|---|---|---|
| | chlofibrate | | | 13.8 ± 3.8 | 9.5 ± 2.5 |
| 1 | H | H | H | 19.3 ± 2.8 | 20.8 ± 3.7 |
| 2 | 4OCH$_3$ | H | H | 21.4 ± 4.2 | 23.5 ± 3.3 |
| 3 | 3CH$_3$ | C$_2$H$_5$ | H | 17.8 ± 3.4 | 18.7 ± 4.5 |
| 4 | 3CH$_3$ | C$_2$H$_5$ | C$_2$H$_5$ | 18.4 ± 2.8 | 18.7 ± 3.6 |
| 5 | 3OCH$_3$ | C$_2$H$_5$ | CH$_3$ | 20.7 ± 7.1 | 17.8 ± 4.4 |
| 6 | 3OCH$_3$ | C$_2$H$_5$ | C$_2$H$_5$ | 19.5 ± 4.7 | 19.6 ± 2.8 |
| 7 | 3OCH$_3$ | H | CH$_3$ | 17.3 ± 2.7 | 18.8 ± 3.3 |
| 8 | 3CH$_3$ | H | CH$_3$ | 18.6 ± | 19.3 ± |

TABLE 2-continued

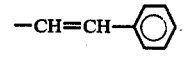

| | Compound | | | Percent Reduction | |
|---|---|---|---|---|---|
| No. | $R_1$ | $R_2$ | $R_3$ | T C $\bar{x} \pm$ S.E. | T G $\bar{x} \pm$ S.E. |
| 9 | 3OCH$_3$ | H | C$_2$H$_5$ | 17.9 ± 3.7 | 18.5 ± 3.4 |
| 10 | 4-OCH$_3$ | CH$_3$ | H | 20.7 ± 2.8 | 24.5 ± 3.1 |
| 11 | 4-OCH$_3$ | C$_3$H$_7$(n) | H | 19.2 ± 1.9 | 21.3 ± 4.2 |
| 12 | 4-OCH$_3$ | C$_4$H$_9$(n) | H | 17.4 ± 3.2 | 19.3 ± 2.9 |
| 13 | 2-Cl | H | H | 14.5 ± 3.5 | 15.2 ± 4.1 |
| 14 | 4-OC$_2$H$_5$ | H | H | 19.5 ± 4.2 | 21.3 ± 2.5 |
| 15 | 2-CH$_3$ | H | H | 17.7 ± 3.4 | 19.4 ± 3.8 |
| 16 | 2,4-(OCH$_3$)$_2$ | C$_2$H$_5$ | C$_2$H$_5$ | 16.4 ± 4.1 | 17.8 ± 2.9 |
| 17 | 2-OCH$_3$ | C$_2$H$_5$ | —CH=CH— | 17.4 ± 3.5 | 19.7 ± 4.5 |
| 18 | 3-OCH$_3$ | C$_2$H$_5$ | 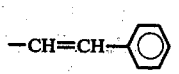 | 18.4 ± 2.9 | 21.3 ± 3.2 |
| 19 | 3-OCH$_3$ | C$_2$H$_5$ | m-CH$_3$C$_6$H$_4$ | 20.1 ± 4.5 | 19.7 ± 3.6 |
| 20 | 3-CH$_3$ | C$_2$H$_5$ | C$_3$H$_7$(n) | 16.5 ± 3.7 | 17.4 ± 4.1 |

EXPERIMENT 3

Platelet rich plasma samples were prepared from the blood of SD strain rats, and to 0.5 ml of the samples, test compounds in the form of a solution in dimethyl sulfoxide (DMSO) were added in such an amount that the concentration of the compounds in the mixture was $1 \times 10^{-4}$ M. The assay media containing aspirin were used as a control. After incubation for one minute, arachidonic acid, collagen and adenosine diphosphate (ADP) were added to the mixture in concentrations of $1 \times 10^{-4}$ M, $1.5 \times 10^{-3}$ M and $1 \times 10^{-6}$ M, respectively, to aggregate the platelets. The aggregation level was determined with an aggregometer, CORNING-EEL MODEL 16P (Manufactured by Evans Electro Selenium Ltd.) and the percent inhibition of platelets was calculated from the following equation:

$$\text{Percent inhibition} = \left(1 - \frac{\text{aggregation level by test compound}}{\text{aggregation level by DMSO alone}}\right) \times 100$$

The results are shown in Table 3 below.

TABLE 3

| Compound | | | | Percent Inhibition of Aggregation (%) | | |
|---|---|---|---|---|---|---|
| No. | $R_1$ | $R_2$ | $R_3$ | Arachidonic acid | Collagen | ADP |
| | aspirin | | | 100 | 8 | 17 |
| 1 | 3CH$_3$ | C$_2$H$_5$ | C$_2$H$_5$ | 60 | 47 | 50 |
| 2 | 3OCH$_3$ | C$_2$H$_5$ | CH$_3$ | 63 | 50 | 45 |
| 3 | 3CH$_3$ | C$_2$H$_5$ | CH$_3$ | 55 | 43 | 50 |
| 4 | 4CH$_3$ | C$_2$H$_5$ | CH$_3$ | 60 | 48 | 51 |
| 5 | 4OCH$_3$ | C$_2$H$_5$ | CH$_3$ | 45 | 30 | 35 |
| 6 | 4OCH$_3$ | C$_2$H$_5$ | H | 40 | 25 | 20 |
| 7 | 4OCH$_3$ | CH$_3$ | H | 38 | 34 | 36 |
| 8 | 4OCH$_3$ | C$_3$H$_7$ | H | 42 | 40 | 43 |
| 9 | 4OCH$_3$ | C$_4$H$_9$ | H | 43 | 37 | 35 |
| 10 | 2,4-(OCH$_3$)$_2$ | C$_2$H$_5$ | C$_2$H$_5$ | 52 | 47 | 44 |
| 11 | 2-OCH$_3$ | C$_2$H$_5$ | —CH=CH— | 48 | 45 | 46 |
| 12 | 3OCH$_3$ | C$_2$H$_5$ | 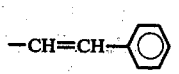 | 50 | 43 | 40 |
| 13 | 3OCH$_3$ | C$_2$H$_5$ | m-CH$_3$·C$_6$H$_4$— | 45 | 41 | 39 |
| 14 | 3CH$_3$ | C$_2$H$_5$ | C$_3$H$_7$ | 60 | 50 | 47 |

EXPERIMENT 4

A solution of a test compound ($5 \times 10^{-4}$ M) was added to one ml of a mixture consisting of 0.9 mg of pig aortic microsomes and $9 \times 10^8$ platelets of SD strain rats. To the mixture, 10 μl of (1-14$_C$)k-arachidonic acid (80 nM, 4.7 Ci/mol) in 0.1 M sodium bicarbonate aqueous solution was added, and after a 3 minutes' reaction at 23° C., 50 μl of 0.5 M citric acid aqueous solution was added to terminate the reaction. To the reaction mixture, 8 ml of ethyl acetate was added and shaked. The organic layer was concentrated to dryness under vacuum, and the residue was dissolved in 100 μl of ethyl acetate, and the solution was subjected to thin-layer chromatography using a silica gel glass plate and a developing solvent made of the upper phase of a 5:11:2:10 mixture of iso-octane/ethyl acetate/acetic adic/water.

After completion of the development, the plate was scanned for radioactivity, and the silica gel in the areas corresponding to radioactive bands of thromboxane $B_2$ and 6-keto-prostaglandin $F_{1\alpha}$ was scrapped and its radioactivity was determined with a liquid scintillation counter. The percent conversion of arachidonic acid to thromboxane $B_2$ or to 6-keto-prostaglandin $F_{1\alpha}$ was calculated, and the amount each of thromboxane $B_2$ and 6-keto-prostaglandin $F_{1\alpha}$ was determined.

Under the conditions described above, all of the $TXA_2$ and $PGI_2$ appeared to be converted into $TXB_2$ and 6-keto-$PGF_{1\alpha}$, respectively. Thus, it can be assumed that the amounts of $TXB_2$ and 6-keto-$PGF_{1\alpha}$ were equated with those of $TXA_2$ and $PGI_2$ formed in the reaction system.

The results are shown in Table 4 wherein the data are based on the amounts of thromboxane $B_2$ and 6-keto-prostaglandin $F_{1\alpha}$ in samples not containing the test compounds. As controls, samples containing imidazole and aspirin were used.

TABLE 4

| Compound | | | Percent Relative Production of | Percent Relative Production of |
|---|---|---|---|---|
| No. | $R_1$ | $R_2$ | $R_3$ | $PGI_2$ | $TXA_2$ |
| | imidazole | | | 3.0 | 0.25 |
| | aspirin | | | 0.1 | 0.1 |
| 1 | 4OCH₃ | H | H | 1.5 | 0.1 |
| 2 | H | H | H | 1.3 | 0.1 |
| 3 | 3OCH₃ | H | CH₃ | 3.5 | 0.35 |
| 4 | 3CH₃ | H | C₂H₅ | 7.0 | 0.25 |
| 5 | 3CH₃ | H | CH₃ | 4.7 | 0.45 |
| 6 | 3OCH₃ | H | C₂H₅ | 3.7 | 0.3 |
| 7 | 2-Cl | H | H | 1.8 | 0.15 |
| 8 | 4OC₂H₅ | H | H | 2.5 | 0.2 |

TABLE 4-continued

| Compound | | | Percent Relative Production of | Percent Relative Production of |
|---|---|---|---|---|
| No. | $R_1$ | $R_2$ | $R_3$ | $PGI_2$ | $TXA_2$ |
| 9 | 2CH₃ | H | H | 3.1 | 0.35 |

EXAMPLE 1

A solution of 1 g of ethyl 10,11-dihydro-4-methoxylbenz[b,f][1,4]oxazepine-8-carboxylate in 30 ml of chloroform was irradiated with natural light for 10 days, and the solvent was distilled off. The residue was subjected to chromatography on silica gel to give 0.85 g of ethyl 4-methoxybenz[b,f][1,4]oxazepine-8-carboxylate. m.p. 95°–96° C.

Elemental analysis: Calculated for $C_{17}H_{15}NO_4$: 68.68 C, 5.09 H, 4.71 N(%); Found: 68.78 C, 5.17 H, 4.82 N(%).

EXAMPLE 2

A mixture of 2 g of ethyl 10,11-dihydro-4-methoxydibenz-[b,f][1,4]oxazepine-8-carboxylate, 2 g of chloranil and 30 ml of xylene was refluxed for 3 hours, and the solvent was distilled off under vacuum. The residue was subjected to chromatography on silica gel to give 1.8 g of ethyl 4-methoxydibenz[b,f][1,4]oxazepine-8-carboxylate. The melting point and elemental analysis of the product were the same as those of a mixture with the product obtained in Example 1.

EXAMPLE 3

The compounds indicated in Table 4 were prepared by repeating the procedures of Examples 1 and 2. The yield data in the Table are those for the products produced by the procedure of Example 1, and similar data were obtained when the procedure of Example 2 was followed. Since the compounds identified as Nos. 9 and 10 were obtained as an oily product, the values for high-resolution mass spectrophotometry are indicated in the column "Elemental analysis" of Table 5, with the values for proton NMR being indicated as footnotes.

TABLE 5

| | Substituent and its position | | Molecular Formula | Yield (%) | m.p. (°C.) | Elemental Analysis | | | | | |
|---|---|---|---|---|---|---|---|---|---|---|---|
| | | | | | | Calculated (%) | | | Found (%) | | |
| No. | $R_1$ | $R_2$ | | | | C | H | N | C | H | N |
| 1 | H | 8-CO₂C₂H₅ | C₁₆H₁₃NO₃ | 87 | 119–121 | 71.90 | 4.90 | 5.24 | 71.79 | 4.94 | 5.20 |
| 2 | 3-OCH₃ | " | C₁₇H₁₅NO₄ | 95 | 107–109 | 68.68 | 5.09 | 4.71 | 68.63 | 5.17 | 4.82 |
| 3 | 2-OCH₃ | " | C₁₇H₁₅NO₄ | 93 | 132–132.5 | 68.68 | 5.09 | 4.71 | 68.71 | 5.22 | 4.82 |
| 4 | 4-OC₂H₅ | " | C₁₈H₁₇NO₄ | 85 | 72–73 | 69.44 | 5.50 | 4.50 | 69.62 | 5.64 | 4.58 |
| 5 | 2-CH₃ | " | C₁₇H₁₅NO₃ | 84 | 126–127.5 | 72.58 | 5.37 | 4.98 | 72.86 | 5.48 | 5.16 |
| 6 | 2-Cl | " | C₁₆H₁₂ClO₃ | 86 | 118–120 | 63.69 | 4.01 | 4.64 | 63.58 | 4.17 | 4.79 |
| 7 | 4-OCH₃ | 8-CO₂CH₃ | C₁₆H₁₃NO₄ | 82 | 164–165 | 67.84 | 4.63 | 4.94 | 67.76 | 4.51 | 5.02 |
| 8 | 4-OC₂H₅ | " | C₁₇H₁₅NO₄ | 87 | 125 | 68.68 | 5.09 | 4.71 | 68.73 | 5.15 | 4.84 |
| 9 | 4-OCH₃ | 8-CO₂C₃H₇(n) | C₁₈H₁₇NO₄ | 90 | oil | 311.1153 | | | mass spectrum*1 311.1162 | | |
| 10 | 4-OCH₃ | 8-CO₂C₄H₉(n) | C₁₉H₁₉NO₄ | 89 | oil | 325.1309 | | | high mass spectrum*2 | | |

TABLE 5-continued

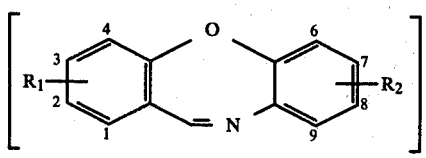

| | Substituent and its position | | Molecular | Yield | m.p. | Elemental Analysis | | | | | |
|---|---|---|---|---|---|---|---|---|---|---|---|
| | | | | | | Calculated (%) | | | Found (%) | | |
| No. | $R_1$ | $R_2$ | Formula | (%) | (°C.) | C | H | N | C | H | N |
| 11 | 4-OCH$_3$ | 8-CO$_2$H | C$_{15}$H$_{11}$NO$_4$ | 63 | 280 (decomposition) | 66.91 | 4.12 | 5.20 | 325.1320 67.09 | 4.07 | 5.16 |

*[1]NMR(CDCl$_3$) δ :8.55(1H,S,11-H), 6.75–8.15(6H, aromatic-H), 4.25(2H,t,J = 6Hz, —CO$_2$CH$_2$CH$_2$CH$_3$), 3.85(3H,S,—OCH$_3$), 1.75(2H, sextet,J = 6Hz, —CO$_2$CH$_2$CH$_2$CH$_3$), 1.0(3H,t,J = 6Hz, —CO$_2$CH$_2$CH$_2$CH$_3$)
*[2]NMR(CDCl$_3$) δ: 8.55(1H,S,11-H), 6.80–8.10(6H, aromatic-H, 4.30(2H,t,J = 6Hz,—CO$_2$CH$_2$CH$_2$CH$_2$CH$_3$), 3.85(3H,S,—OCH$_3$), 2.0–0.80(7H,br,—CO$_2$CH$_2$CH$_2$CH$_2$CH$_3$)

EXAMPLE 4

A mixture of 8.3 g of ethyl 3-acetylamino-4-(3-methoxyphenoxy)-benzoate and 15.4 g of phosphorus oxychloride and 50 ml of dried toluene was refluxed for 3 hours. The mixture was then cooled and the precipitating crystal was filtered and washed with ethyl acetate to give 8.2 g of ethyl 11-methyl-3-methoxydibenz[b,f][1,4]oxazepine-8-carboxylate hydrochloride. The product was neutralized with ammonia water and extracted with ethyl acetate. After concentrating the extract, ethanol was added to the residue and the precipitating crystal was recrystallized from ethanol to give 6.9 g of ethyl 11-methyl-3-methoxydibenz[b,f][1,-4]oxazepine-8-carboxylate as a colorless acicular crystal.

Yield 88%, m.p. 117°–118° C.

Elemental analysis: Calculated for C$_{18}$H$_{17}$NO$_4$: 69.44 C, 5.50 H, 4.50 N(%); Found: 69.48 C, 5.56 H, 4.43N(%).

The compounds indicated in Tables 6 and 7 were produced by repeating the same procedure as above.

TABLE 6

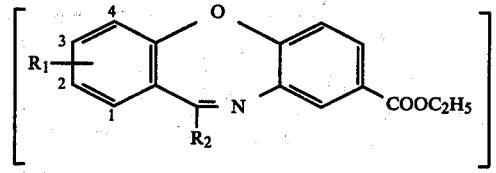

| | Substituent and its position | | Molecular | Yield | m.p. | Elemental Analysis | | | | | |
|---|---|---|---|---|---|---|---|---|---|---|---|
| | | | | | | Calculated (%) | | | Found (%) | | |
| No. | $R_1$ | $R_2$ | Formula | (%) | (°C.) | C | H | N | C | H | N |
| 1 | 2-OCH$_3$ | CH$_3$ | C$_{18}$H$_{17}$NO$_4$ | 65 | 130–131 | 69.44 | 5.50 | 4.50 | 69.39 | 5.52 | 4.43 |
| 2 | 3-OCH$_3$ | C$_2$H$_5$ | C$_{19}$H$_{19}$NO$_4$ | 93 | 61–62.5 | 70.14 | 5.89 | 4.30 | 70.10 | 5.82 | 4.33 |
| 3 | 2-OCH$_3$ | C$_6$H$_5$ | C$_{23}$H$_{19}$NO$_4$ | 80 | 102–103 | 73.98 | 5.13 | 3.75 | 73.97 | 5.11 | 3.68 |
| 4 | 3-OCH$_3$ | " | " | 95 | 132–133 | " | | | 73.89 | 5.15 | 3.69 |
| 5 | 4-OCH$_3$ | " | " | 70 | 155–156 | " | | | 73.90 | 5.12 | 3.73 |
| 6 | 2-OCH$_3$ | CH=CHC$_6$H$_5$ | C$_{25}$H$_{21}$NO$_4$ | 68 | 120–130 | 75.17 | 5.30 | 3.51 | 75.15 | 5.20 | 3.48 |
| 7 | 3-OCH$_3$ | " | " | 71 | 120.5–12-1.5 | " | | | 75.21 | 5.25 | 3.42 |
| 8 | 4-OCH$_3$ | " | " | 53 | 87–89 | " | | | 75.20 | 5.38 | 3.39 |
| 9 | 3-OCH$_3$ | m-CH$_3$C$_6$H$_4$ | C$_{24}$H$_{21}$NO$_4$ | 93 | 172.5–17-3.5 | 74.40 | 5.46 | 3.62 | 74.36 | 5.48 | 3.60 |
| 10 | 4-OCH$_3$ | " | " | 81 | 179–180 | " | | | 74.36 | 5.45 | 3.59 |
| 11 | 2,4-(OCH$_3$)$_2$ | C$_2$H$_5$ | C$_{20}$H$_{21}$NO$_5$ | 88 | 133–135 | 67.59 | 5.96 | 3.94 | 67.63 | 5.90 | 3.88 |
| 12 | " | C$_6$H$_5$ | C$_{24}$H$_{21}$NO$_5$ | 92 | 137–138 | 71.45 | 5.25 | 3.47 | 71.40 | 5.23 | 3.45 |
| 13 | 3-CH$_3$ | CH$_3$ | C$_{18}$H$_{17}$NO$_3$ | 75 | 111–112 | 73.20 | 5.80 | 4.74 | 73.13 | 5.76 | 4.71 |
| 14 | 3-CH$_3$ | C$_2$H$_5$ | C$_{19}$H$_{19}$NO$_3$ | 79 | 41–43 | 73.77 | 6.19 | 4.53 | 73.72 | 6.18 | 4.45 |
| 15 | 4-CH$_3$ | " | C$_{19}$H$_{20}$Cl-NO$_3$ | 62 | 115–117 | 65.99 | 5.83 | 4.05 | 65.90 | 5.90 | 4.01 |
| 16 | 3-CH$_3$ | n-C$_3$H$_7$ | C$_{20}$H$_{22}$Cl-NO$_3$ | 73 | 139–141 | 66.75 | 6.16 | 3.89 | 66.73 | 6.20 | 3.81 |
| 17 | 2-CH$_3$ | C$_6$H$_5$ | C$_{23}$H$_{19}$NO$_3$ | 67 | 104–106 | 77.29 | 5.36 | 3.92 | 77.35 | 5.37 | 3.87 |
| 18 | 3-CH$_3$ | C$_6$H$_5$ | C$_{23}$H$_{19}$NO$_3$ | 88 | 139–140 | 77.29 | 5.36 | 3.92 | 77.24 | 5.35 | 3.85 |
| 19 | 4-CH$_3$ | " | " | 85 | 135–136 | " | | | 77.30 | 5.33 | 3.87 |
| 20 | 2-CH$_3$ | m-CH$_3$C$_6$H$_4$ | C$_{24}$H$_{21}$NO$_3$ | 82 | 128–129 | 77.61 | 5.70 | 3.77 | 77.49 | 5.75 | 3.71 |

TABLE 7

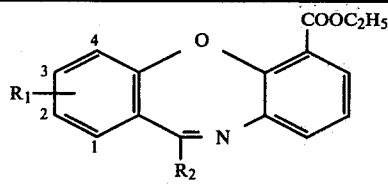

| No. | Substituent and its position R₁ | R₂ | Molecular Formula | Yield (%) | m.p. (°C) | Calculated (%) C | H | N | Found (%) C | H | N |
|---|---|---|---|---|---|---|---|---|---|---|---|
| 1 | 3-OCH₃ | C₂H₅ | C₁₉H₁₉NO₄ 1/2 H₂SO₄ | 81 | 191–192 | 60.95 | 5.39 | 3.74 | 60.77 | 5.28 | 3.54 |
| 2 | 3-OCH₃ | p-CH₃—C₆H₄ | C₂₄H₂₁NO₄ | 90 | 111–112 | 74.40 | 5.64 | 3.62 | 74.32 | 5.51 | 3.47 |

EXAMPLE 5

A mixture of 1 g of ethyl 11-methyl-3-methoxydibenz-[b,f][1,4]oxazepine-8-carboxylate, 10 ml of methanol and 10 ml of 1 N aqueous sodium hydroxide was refluxed for 1 hour. After cooling, the mixture was neutralized with diluted hydrochloric acid, and the precipitating crystal was filtered off and recrystallized from methanol to give 0.84 g of 11-methyl-3-methoxydibenz[b,f][1,4]oxazepine-8-carboxylic acid. Yield 92%, m.p. 247° C. (with decomposition).

Elemental analysis: Calculated for $C_{16}H_{13}NO_4$: 67.84 C, 4.63 H, 4.94 N(%); Found: 67.82 C, 4.61 H, 4.90 N(%).

The compounds indicated in Table 8 were prepared by repeating the same procedure as above.

TABLE 7

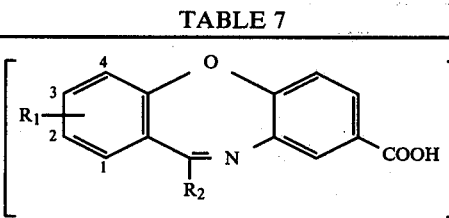

| No. | Substituent and its position R₁ | R₂ | Molecular Formula | Yield (%) | m.p. (°C) | Calculated (%) C | H | N | Found (%) C | H | N |
|---|---|---|---|---|---|---|---|---|---|---|---|
| 1 | 4-OCH₃ | m-CH₃C₆H₄ | C₂₂H₁₇NO₄ | 91 | 246–247 | 73.57 | 4.77 | 3.90 | 73.48 | 4.70 | 3.83 |
| 2 | 4-CH₃ | C₆H₅ | C₂₁H₁₅NO₃ | 92 | 275–277 | 76.58 | 4.59 | 4.25 | 76.60 | 4.65 | 4.20 |
| 3 | 3-OCH₃ | C₂H₅ | C₁₇H₁₅NO₄ | 90 | 248–250 | 68.68 | 5.09 | 4.71 | 68.59 | 5.05 | 4.76 |
| 4 | " | m-CH₃C₆H₄ | C₂₂H₁₇NO₄ | 95 | 229–230 | 76.07 | 4.93 | 4.03 | 76.01 | 4.93 | 4.00 |
| 5 | " | CH=CHC₆H₅ | C₂₃H₁₇NO₄ | 93 | 250 (decomposition) | 74.38 | 4.61 | 3.77 | 74.31 | 4.50 | 3.72 |
| 6 | 3-CH₃ | CH₃ | C₁₆H₁₃NO₃ | 93 | 230–232 | 71.90 | 4.90 | 5.24 | 71.89 | 4.95 | 5.19 |
| 7 | 3-CH₃ | C₂H₅ | C₁₇H₁₅NO₃ | 90 | 211–213 | 72.58 | 5.37 | 4.98 | 72.53 | 5.38 | 4.89 |

What is claimed is:

1. A dibenzoxazepine derivative of the formula:

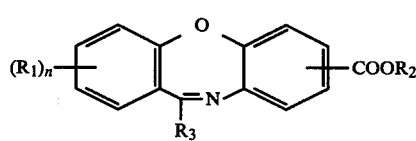

(I)

wherein the carboxy substituent is in the 6- or 8-position; R₁ is a hydrogen atom, a halogen atom, a lower alkyl group or a lower alkoxy group; n is an integer of 1 or 2 provided that each R₁ is the same or different when n is 2; R₂ is a hydrogen atom or a lower alkyl group; R₃ is a lower alkyl group, a phenyl group which may have a m-CH₃ group substituent or a styryl group; or a pharmaceutically acceptable salt thereof.

2. A dibenzoxazepine derivative of the formula:

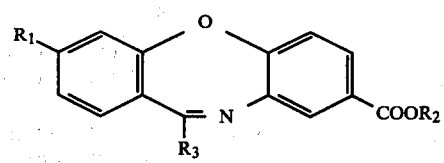

wherein R₁ is a lower alkyl group or a lower alkoxyl group; R₂ is a hydrogen atom or a lower alkyl group; R₃ is a lower alkyl group or a pharmaceutically acceptable salt thereof.

3. A dibenzoxazepine derivative of the formula:

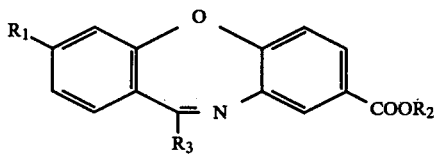

wherein R₁ is methyl or methoxy; R₂ is a hydrogen atom, methyl or ethyl; R₃ is methyl or ethyl; or a pharmaceutically acceptable salt thereof.

4. 11-Ethyl-3-methoxydibenz[b,f][1,4]oxazepine-8-carboxylic acid according to claim 2.

5. Ethyl 11-methyl-3-methoxydibenz[b,f][1,4]oxazepine-8-carboxylate according to claim 2.

6. 3,11-Dimethyldibenz[b,f][1,4]oxazepine-8-carboxylic acid according to claim 2.

7. Ethyl 3,11-dimethyldibenz[b,f][1,4]oxazepine-8-carboxylate according to claim 2.

8. 11-Methyl-3-methoxydibenz[b,f][1,4]oxazepine-8-carboxylic acid according to claim 2.

9. Ethyl 11-ethyl-3-methoxydibenz[b,f][1,4]oxazepine-8-carboxylate according to claim 2.

10. 11-Ethyl-3-methyldibenz[b,f][1,4]oxazepine-8-carboxylic acid according to claim 2.

11. Ethyl 11-ethyl-3-methyldibenz[b,f][1,4]oxazepine-8-carboxylate according to claim 2.

12. Ethyl 11-n-propyl-3-methyldibenz[b,f][1,4]oxazepine-8-carboxylate according to claim 2.

13. A pharmaceutical composition for treating diseases in circulatory organs comprising a dibenzoxzepine derivative of the formula:

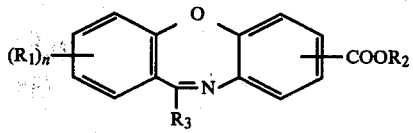

wherein the carboxy group is in the 6- or 8-position; $R_1$ is a hydrogen atom, a halogen atom, a lower alkyl group or a lower alkoxyl group; n is an integer of 1 or 2 provided that each $R_1$ may be different when n is 2; $R_2$ is a hydrogen atom or a lower alkyl group; $R_3$ is, a lower alkyl group, a phenyl group which may have a m-$CH_3$ group as substituent or a styryl group; or a pharmaceutically acceptable excipient.

14. A composition according to claim 13 which is formulated in the form of a tablet, granule, powder or capsule suitable for oral administration.

15. A composition according to claim 14 which contains as an excipient lactose, starch, dextrin, sucrose, crystalline cellulose, kaolin, calcium carbonate, talc or magnesium stearate.

16. A composition according to claim 13 which is formulated in a form suitable for injection.

17. A composition according to claim 16 which contains as a diluent a salt solution selected from the group consisting of aqueous solution bicarbonate and aqueous potassium bicarbonate.

18. A method for treating diseases in circulatory organs which comprises administering to a patient in need of said therapy an amount effective for said therapy of a compound according to claim 1.

19. A method according to claim 18, wherein the composition is administered in an amount of from 1 to 2,000 mg per day of the pharmaceutically active compound.

20. A method according to claim 18, wherein the composition is administered in an amount of from 5 to 800 mg per day of the pharmaceutically active compound.

* * * * *